United States Patent [19]

Nair

[11] Patent Number: 5,236,949
[45] Date of Patent: Aug. 17, 1993

[54] METHOD FOR CONTROLLING INSECTS

[75] Inventor: Muraleedharan G. Nair, Okemos, Mich.

[73] Assignee: Board of Trustees operating Michigan State University, East Lansing, Mich.

[21] Appl. No.: 11,512

[22] Filed: Feb. 1, 1993

Related U.S. Application Data

[60] Division of Ser. No. 811,950, Dec. 23, 1991, which is a continuation-in-part of Ser. No. 177,311, Apr. 5, 1988, abandoned.

[51] Int. Cl.$^5$ ............................................. A01N 43/16
[52] U.S. Cl. ..................................................... 514/459
[58] Field of Search ........................................... 514/459

[56] References Cited

U.S. PATENT DOCUMENTS 3,116,202 12/1963 Dietz et al. ............................ 167/65
4,225,674 9/1980 Celmer et al. ....................... 435/122
4,247,462 1/1981 Celmer et al. ................. 260/239.3 P

OTHER PUBLICATIONS

Hirata, Y., et al., Tet. Let. 14 252-254 (1961).
Yamazaki, M., et al., Tet. Let. 26 2701-2704 (1972).
Kakinuma, K., et al., Tetrahedron 217-222 (1976).
Koyama, Y., et al., Tet. Let. 5 355-358 (1969).

*Primary Examiner*—Allen J. Robinson
*Attorney, Agent, or Firm*—Ian C. McLeod

[57] ABSTRACT

A method for controlling insects using nitrophenyl pyrones is described. The pyrones are preferably derived from Streptomyces sp. by a method involving growth and extraction of the pyrones. A novel pyrone, griseulin is also described.

14 Claims, 17 Drawing Sheets

5,236,949

METHOD FOR CONTROLLING INSECTS

CROSS-REFERENCED TO RELATED APPLICATIONS

This is a divisional of copending application Ser. No. 07/811,950 filed on Dec. 23, 1991, which is a continuation-in-part of application Ser. No. 07/177,311, filed Apr. 5, 1988 now abandoned.

BACKGROUND OF THE INVENTION (1) Field of the Invention

The present invention relates to a method for controlling pests wherein the insect is exposed to a pyrone containing a nitrophenyl group. The compounds are particularly effective against nematodes and mosquito larvae.

(2) Prior Art

Many nitrophenyl pyrones of the present invention are known compounds. Aureothin is described by Hirata, Y., et al., Tet. Let. 14 252-254 (1961) and Yamazaki, M., et al., Tet. Let. 26 2701-2704 (1972). Spectinabilin is described by Kakinuma, K, et al Tetrahedron 217-222 (1976) as having antibacterial activity. Luteoreticulin is described by Kovama, Y, et al., Tet. Let. 5 355-358 (1969).

U.S. Pat. Nos. 3,116,202 to Dietz et al 4,225,674 to Celmer et al and 4,247,462 to Celmer et al describe species of Streptomyces which produce a streptovaricin, an antibacterial compound. It is known that these fungi can produce other compounds besides the ansamycin antibacterial. Thus, Kakinuma et al Tetrahedron (1976) showed that spectinabilin is produced by the same strain which produces the streptovaricin antibiotics.

The problem faced by the prior art is to provide potent insecticidal compounds which are effective at low dosages.

OBJECTS

It is therefore an object of the present invention to provide a particularly effective method for controlling insects. It is further an object to provide a method which requires low dosages of the insecticidal compounds and thus is economical. These and other objects will become increasingly apparent by reference to the following description and the drawings.

IN THE DRAWINGS

GENERAL DESCRIPTION

Figure 1:
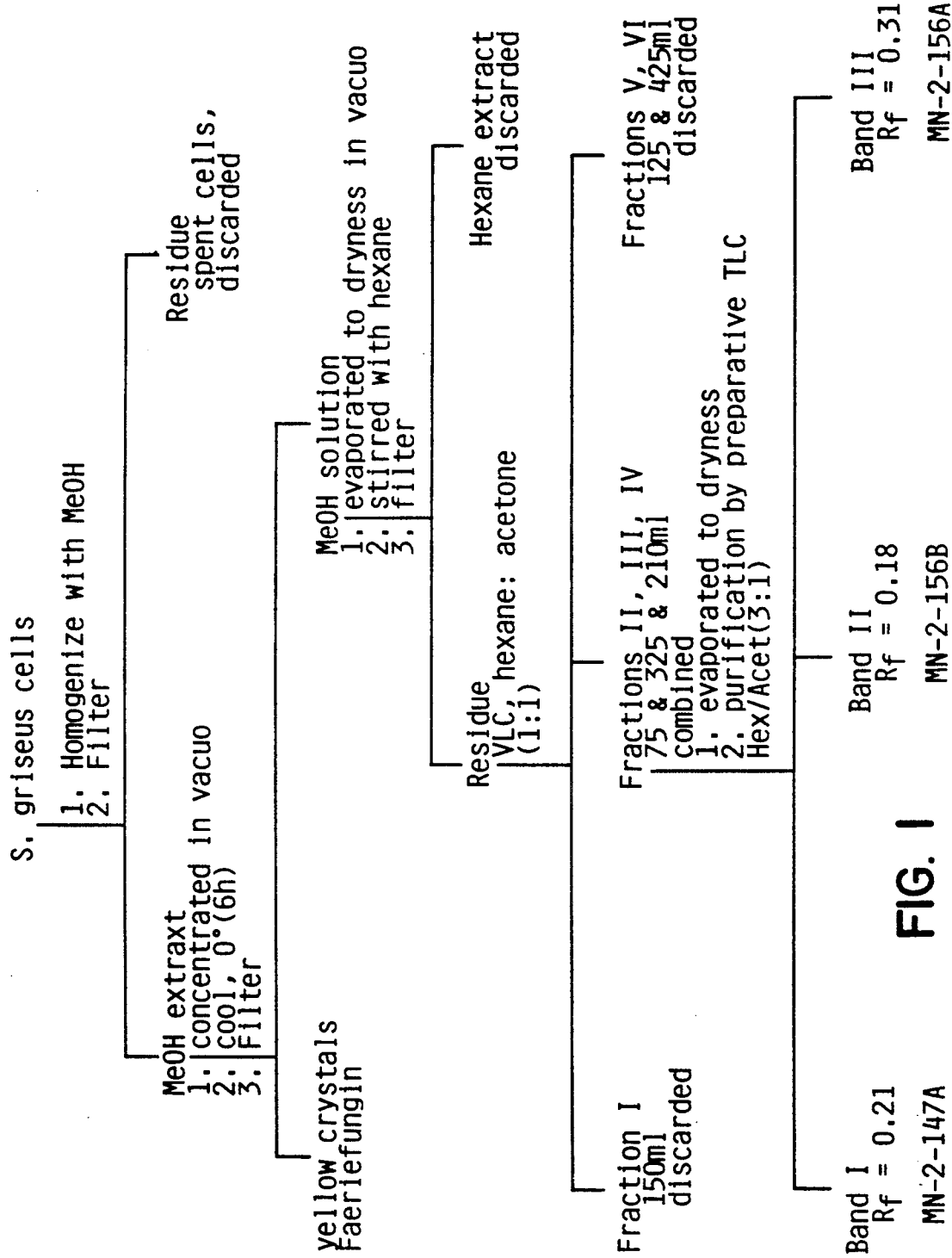
FIG. 1 is a diagram showing the sequence for the extraction of the nitrophenyl pyrones of Examples 1 to 4.
Figure 2:
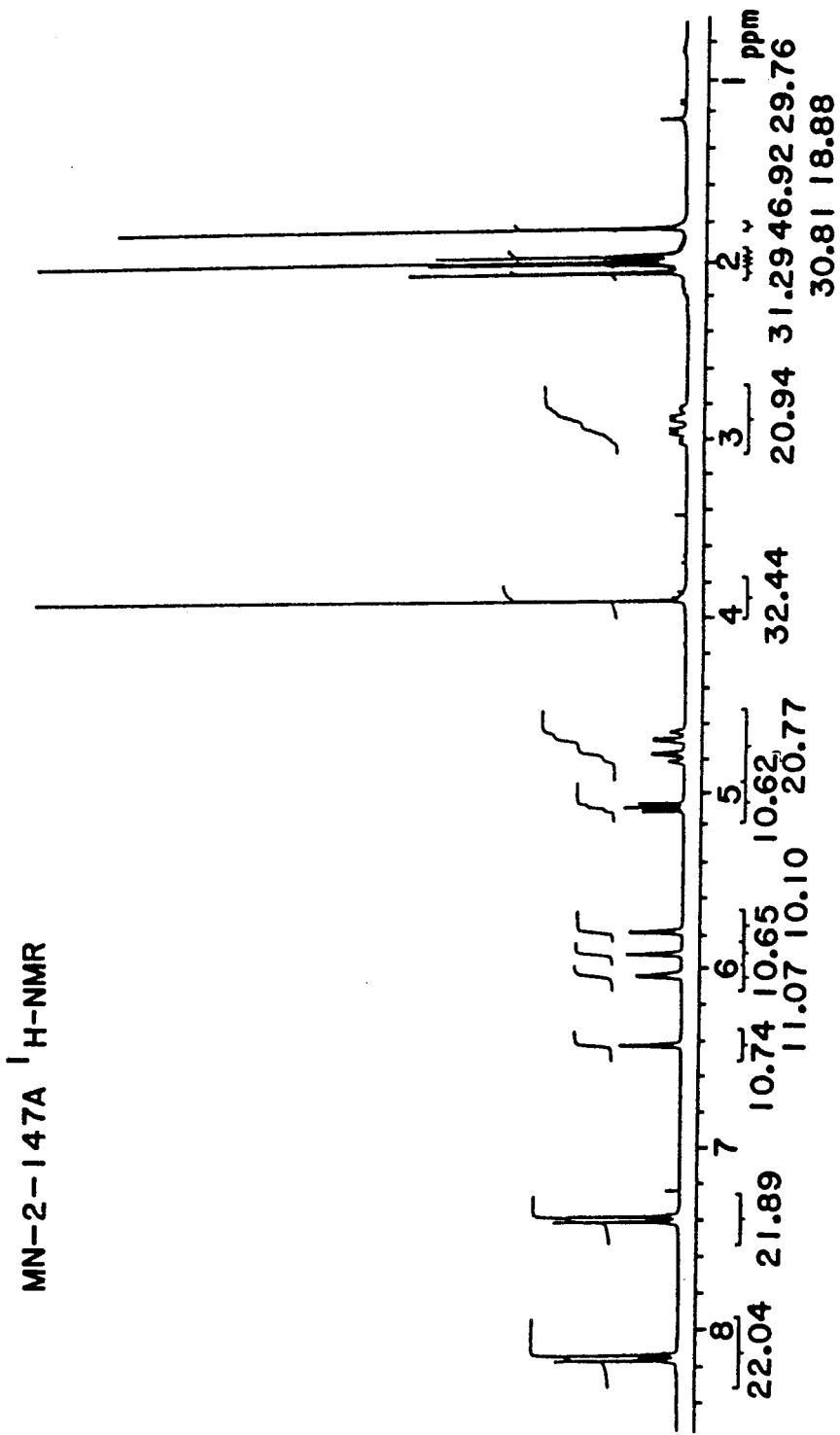
FIGS. 2 to 5 are $^1$H-NMR spectra for the nitrophenyl pyrones of Examples 1 to 4.
Figure 3:
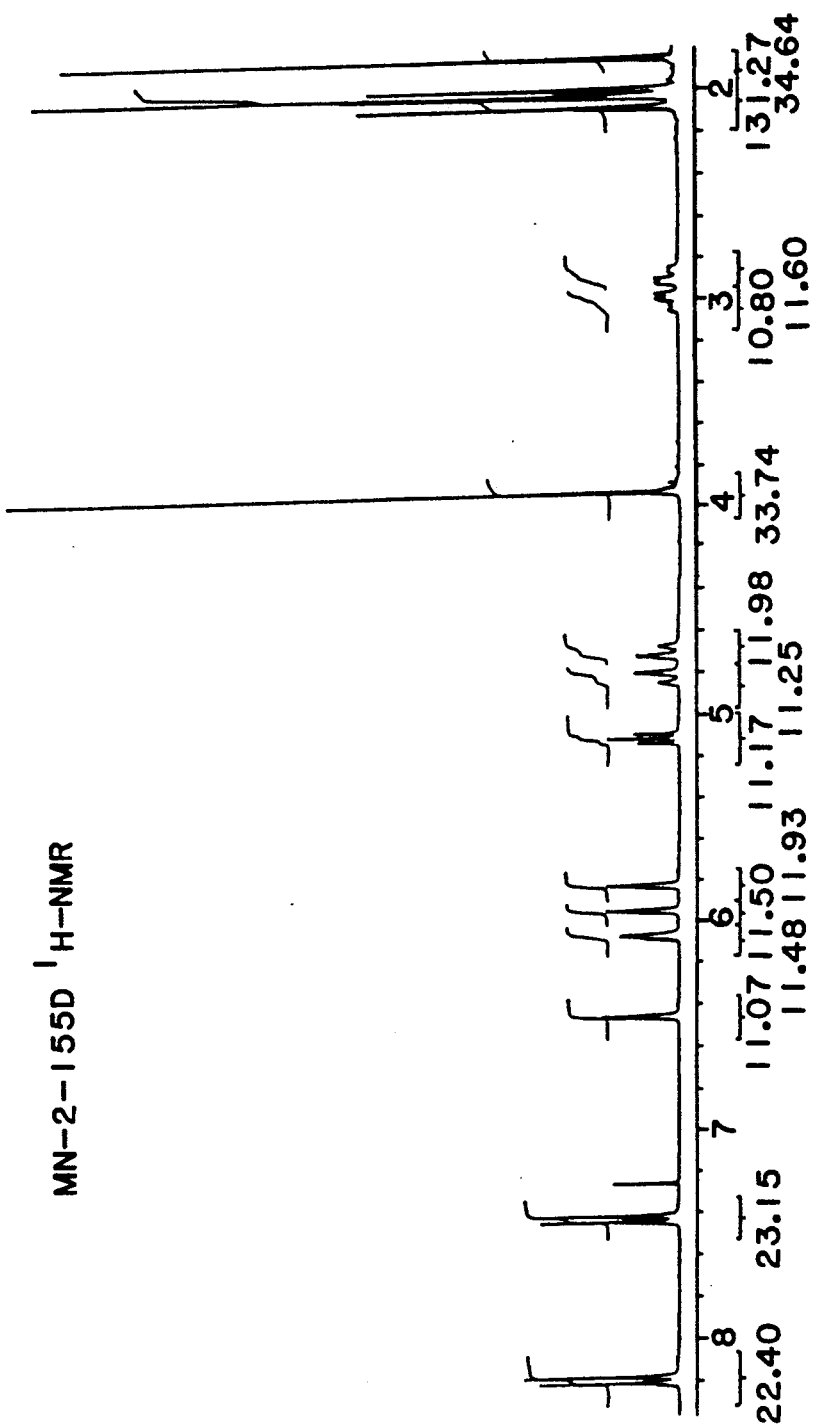
Figure 4:
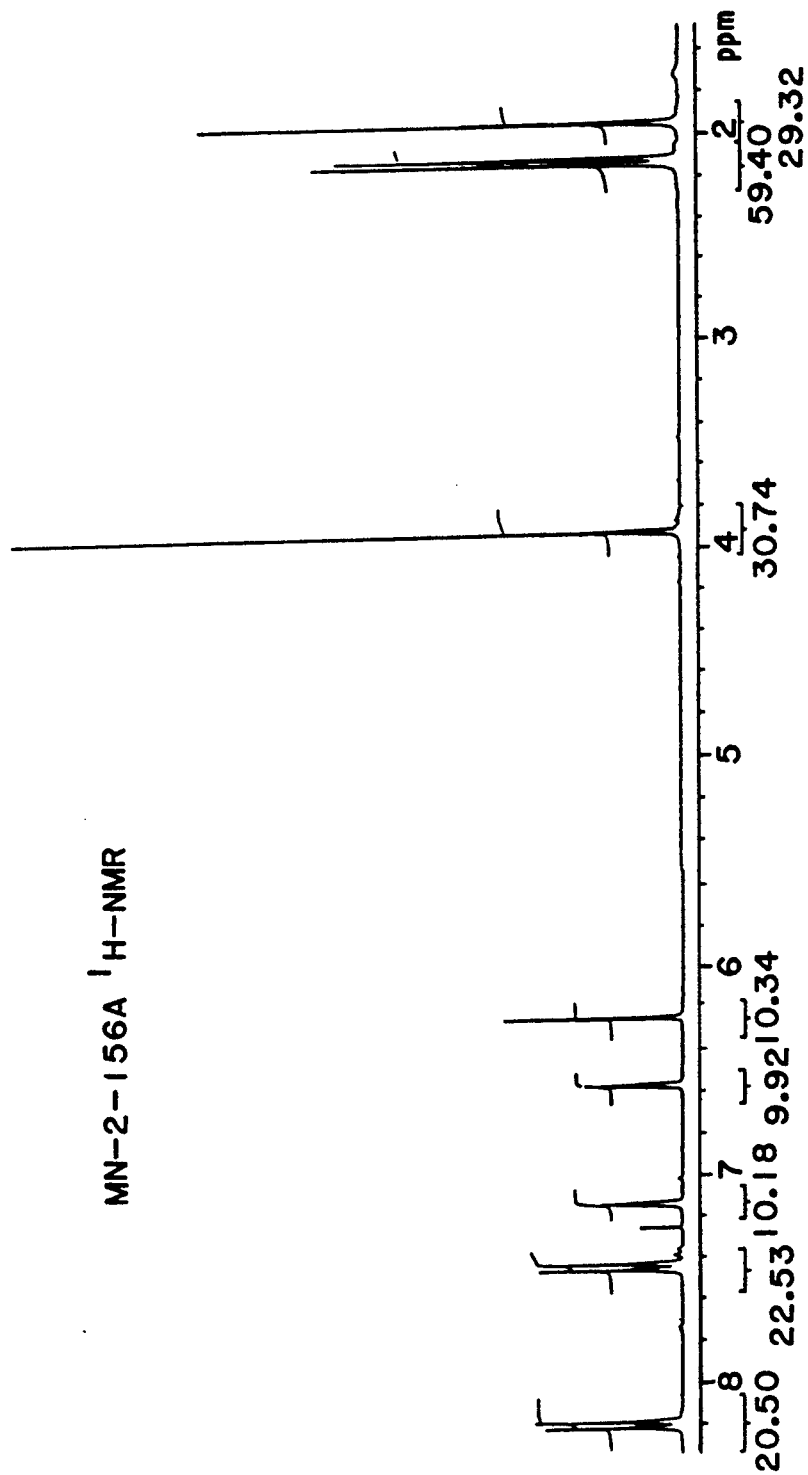
Figure 5:
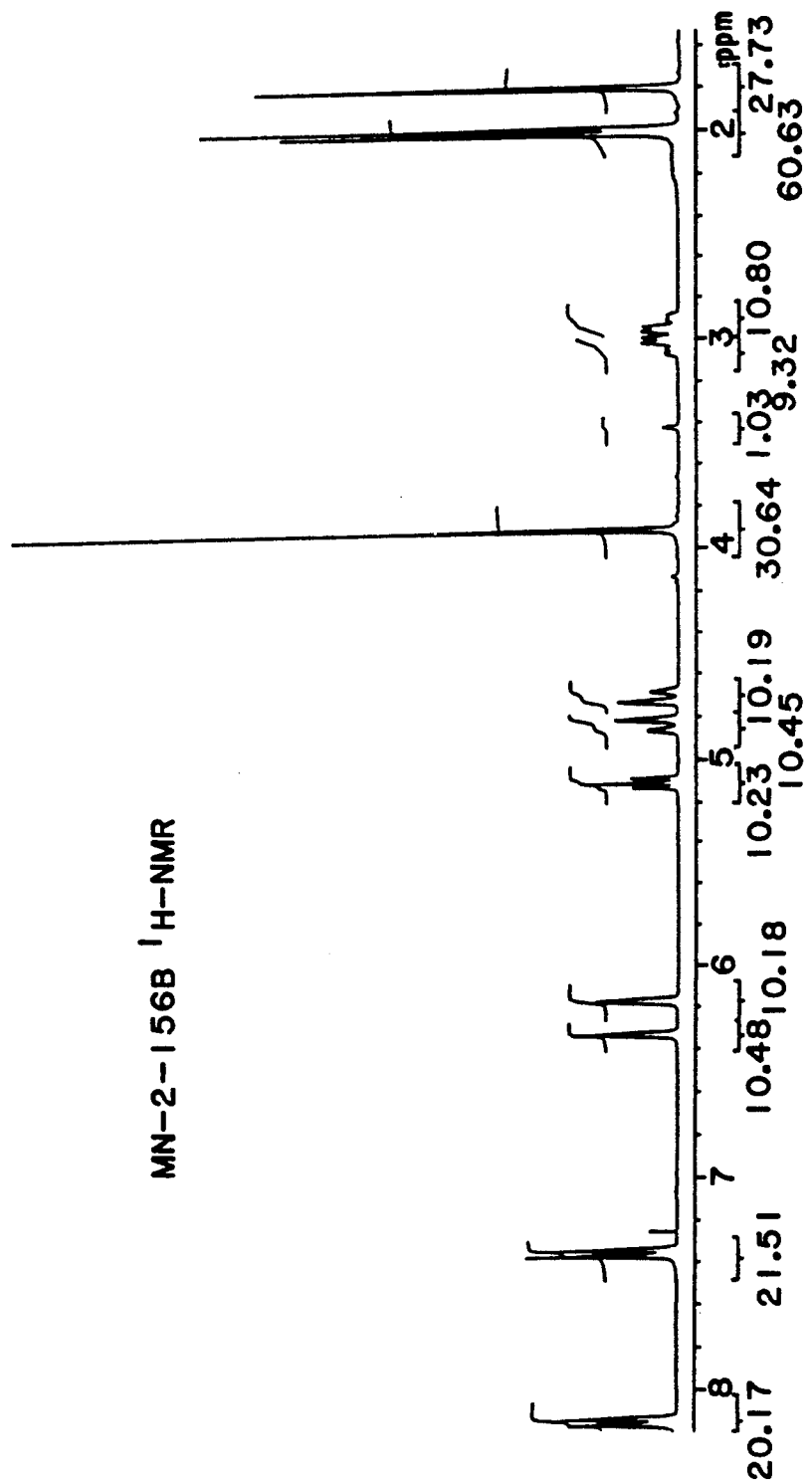
Figure 6:
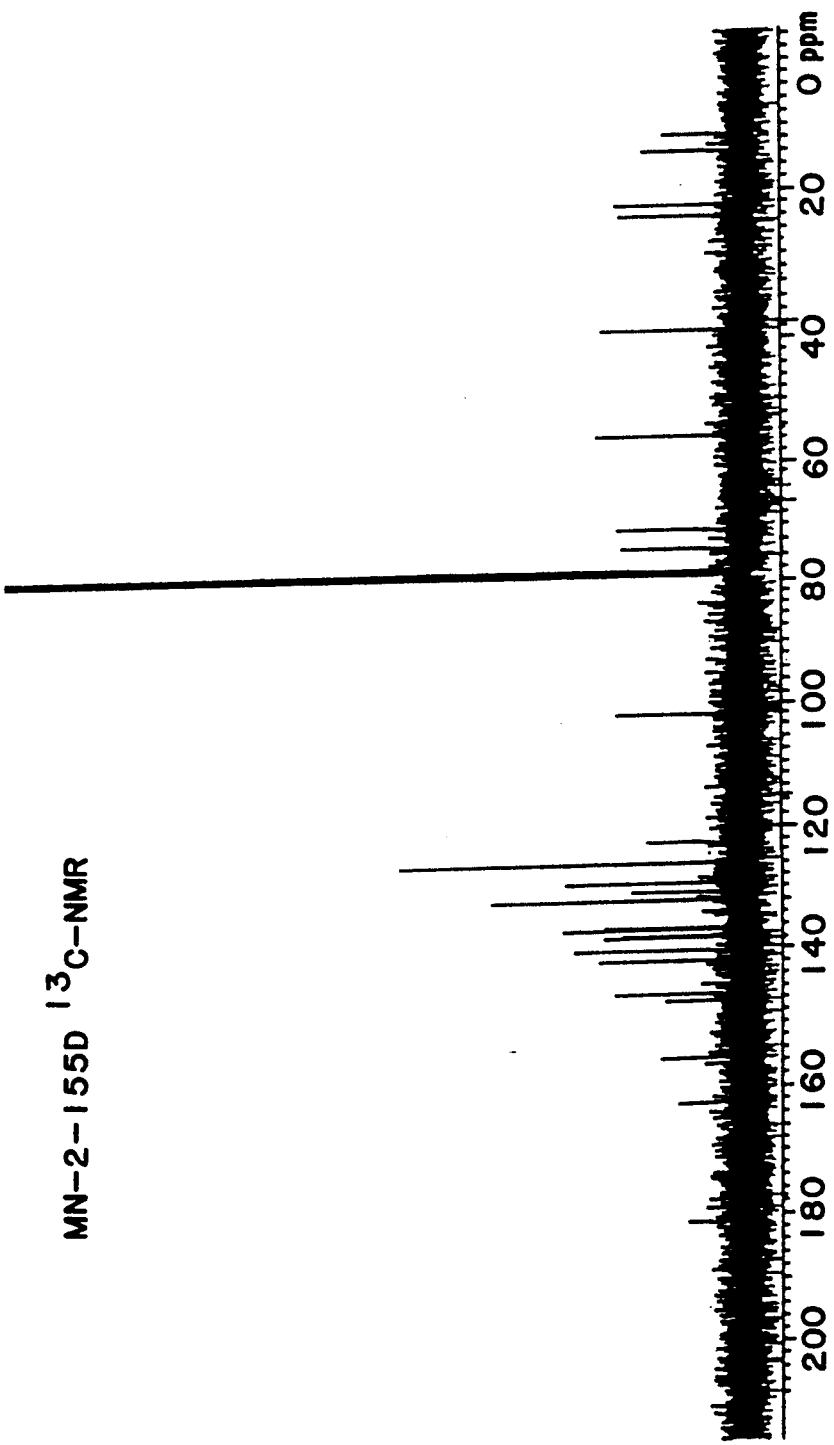
FIGS. 6 to 9 are $^{13}$C-NMR spectra for the nitrophenyl pyrones of Examples 1 to 4.
Figure 7:
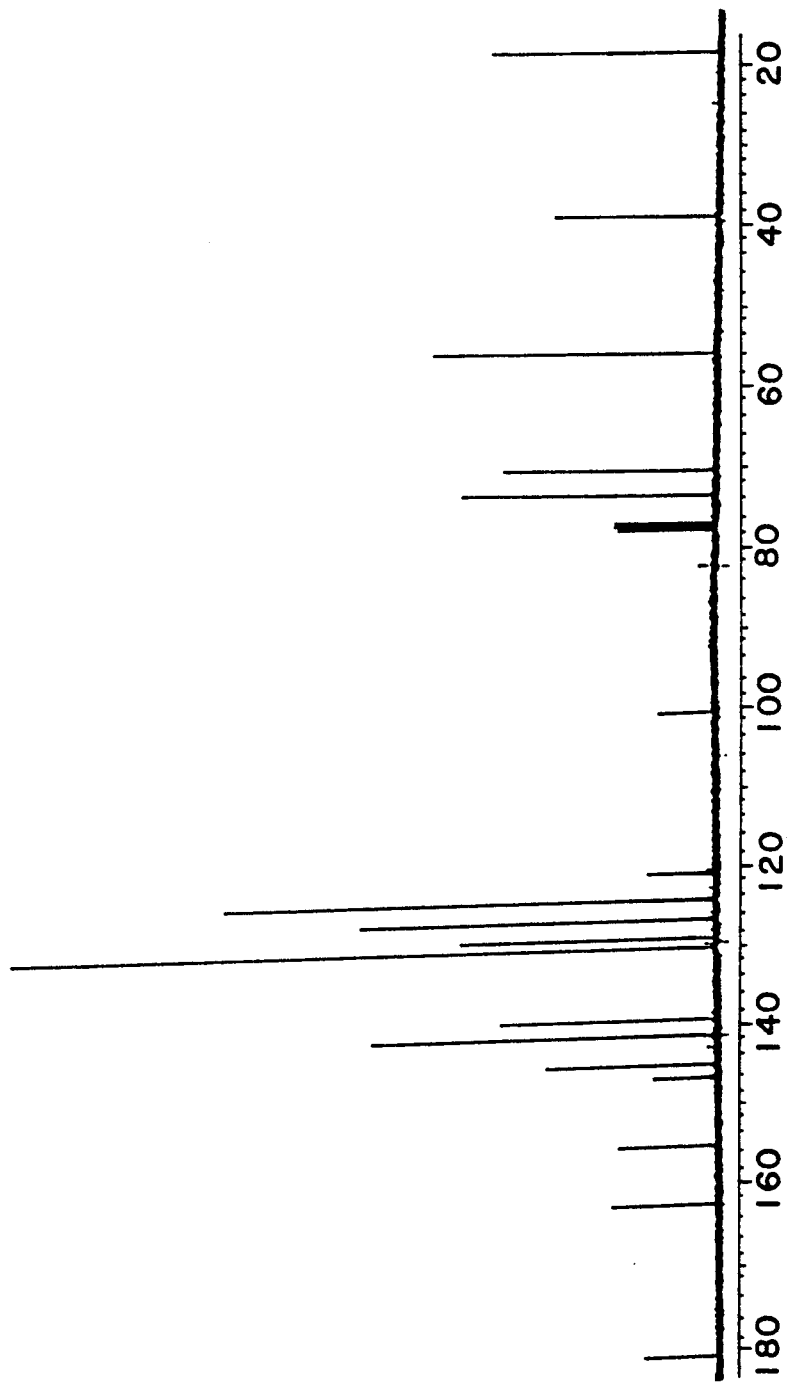
Figure 8:
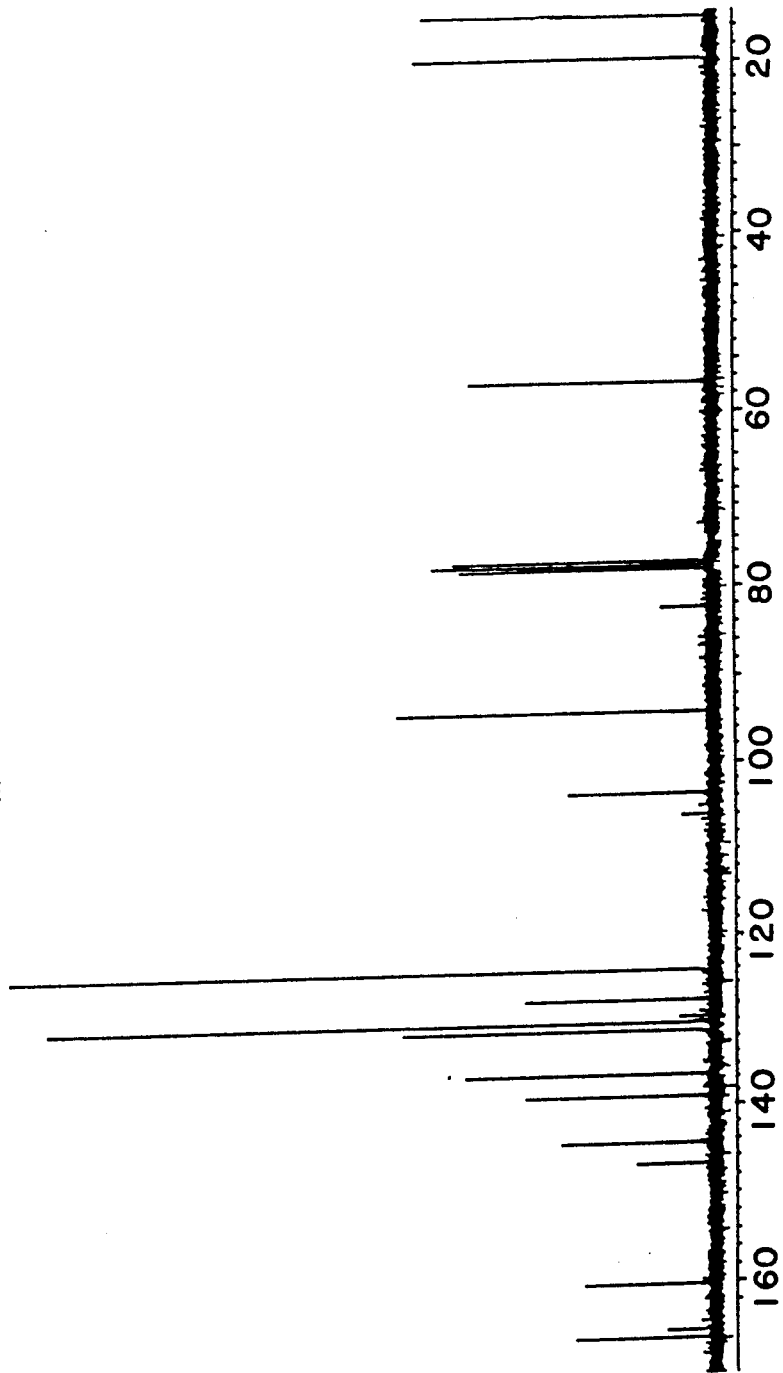
Figure 9:
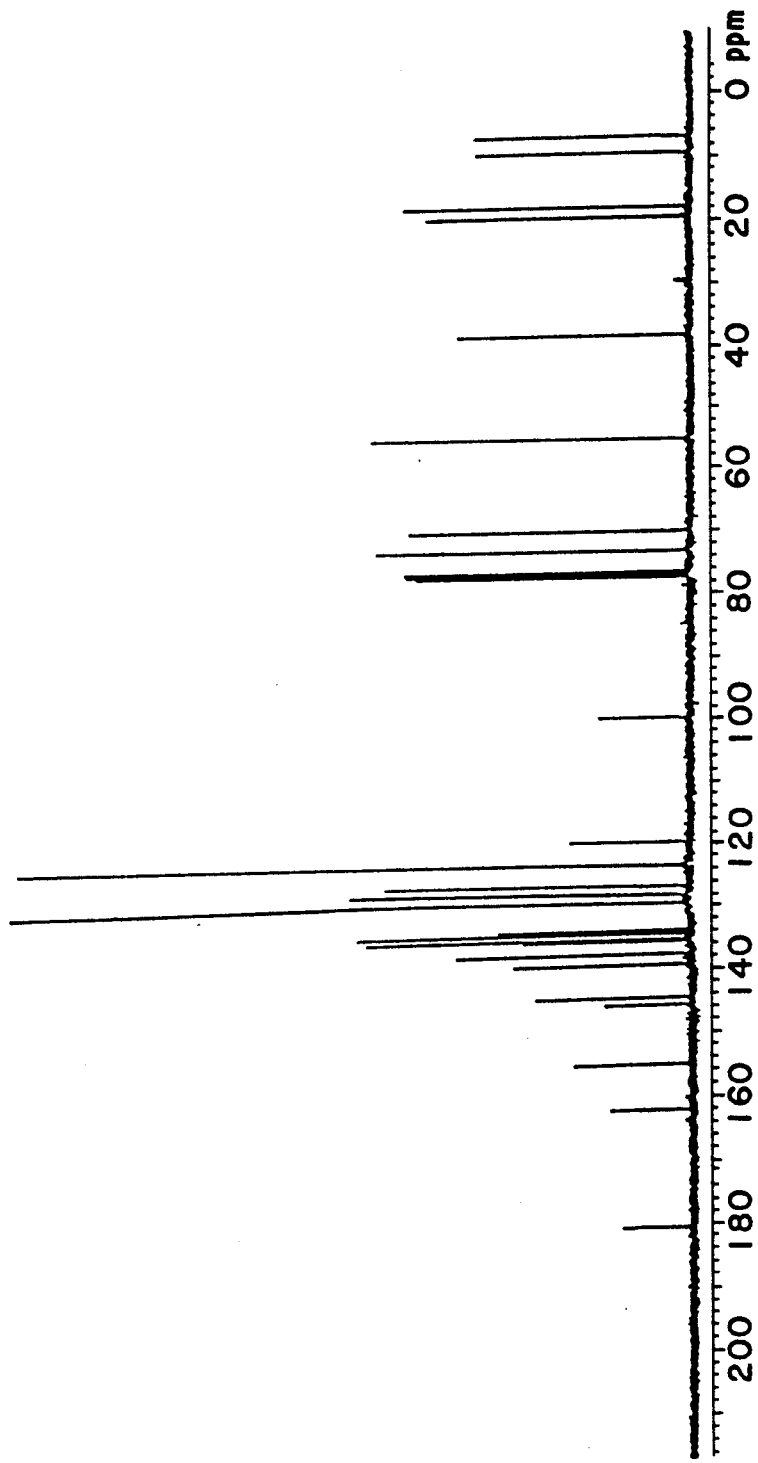
Figure 10:
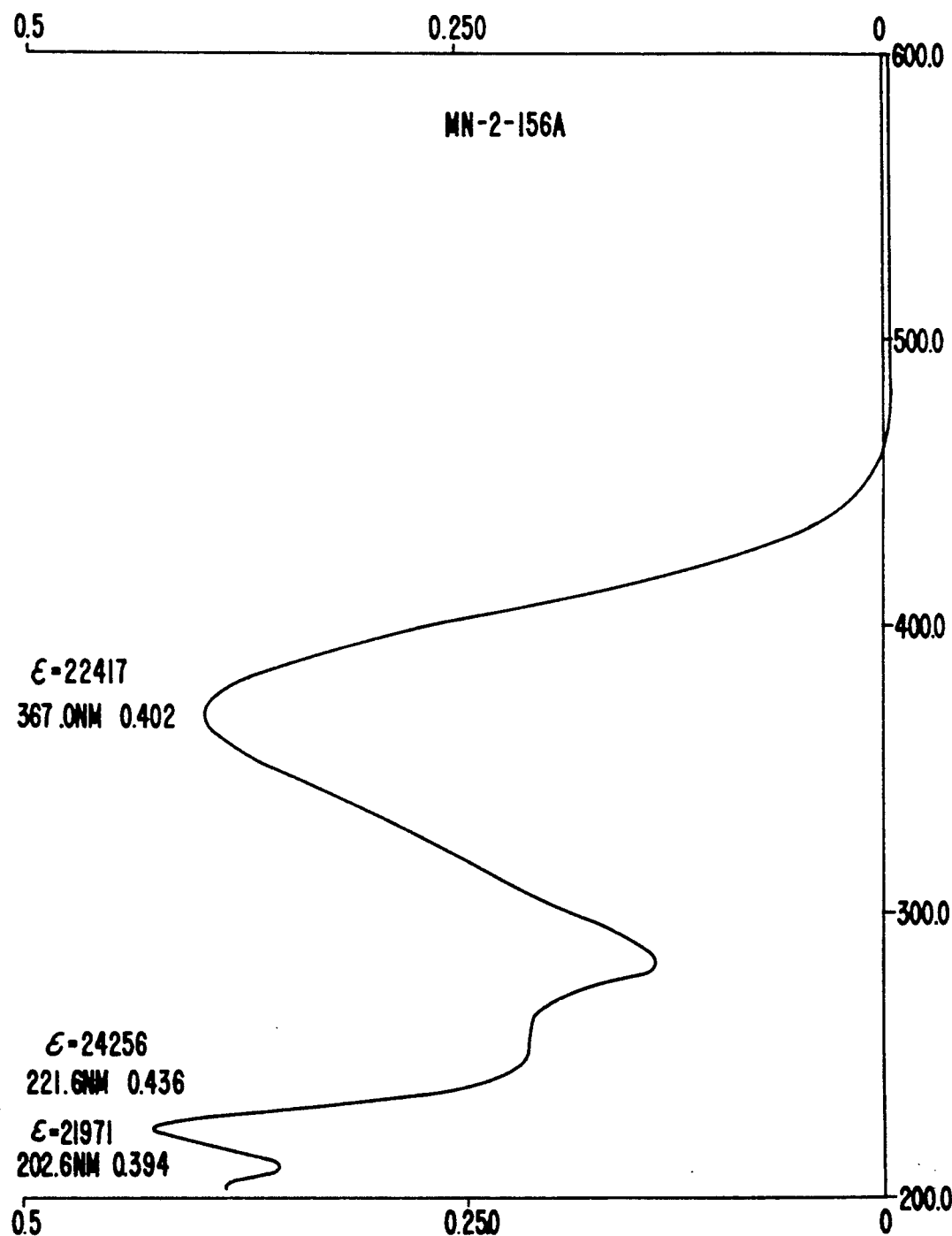
FIGS. 10 to 13 are ultraviolet spectra for the nitrophenyl pyrones of Examples 1 to 4.
Figure 11:
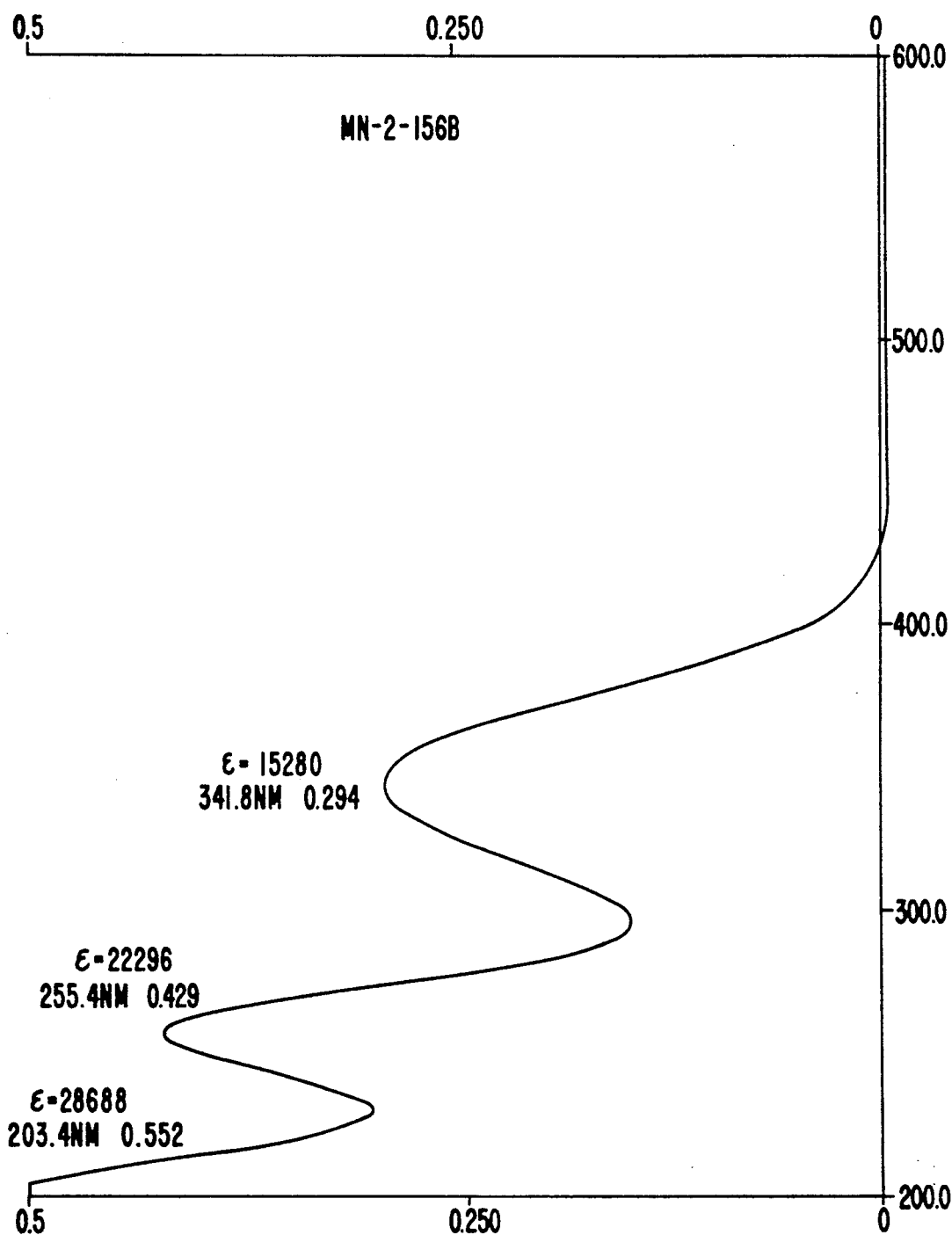
Figure 12:
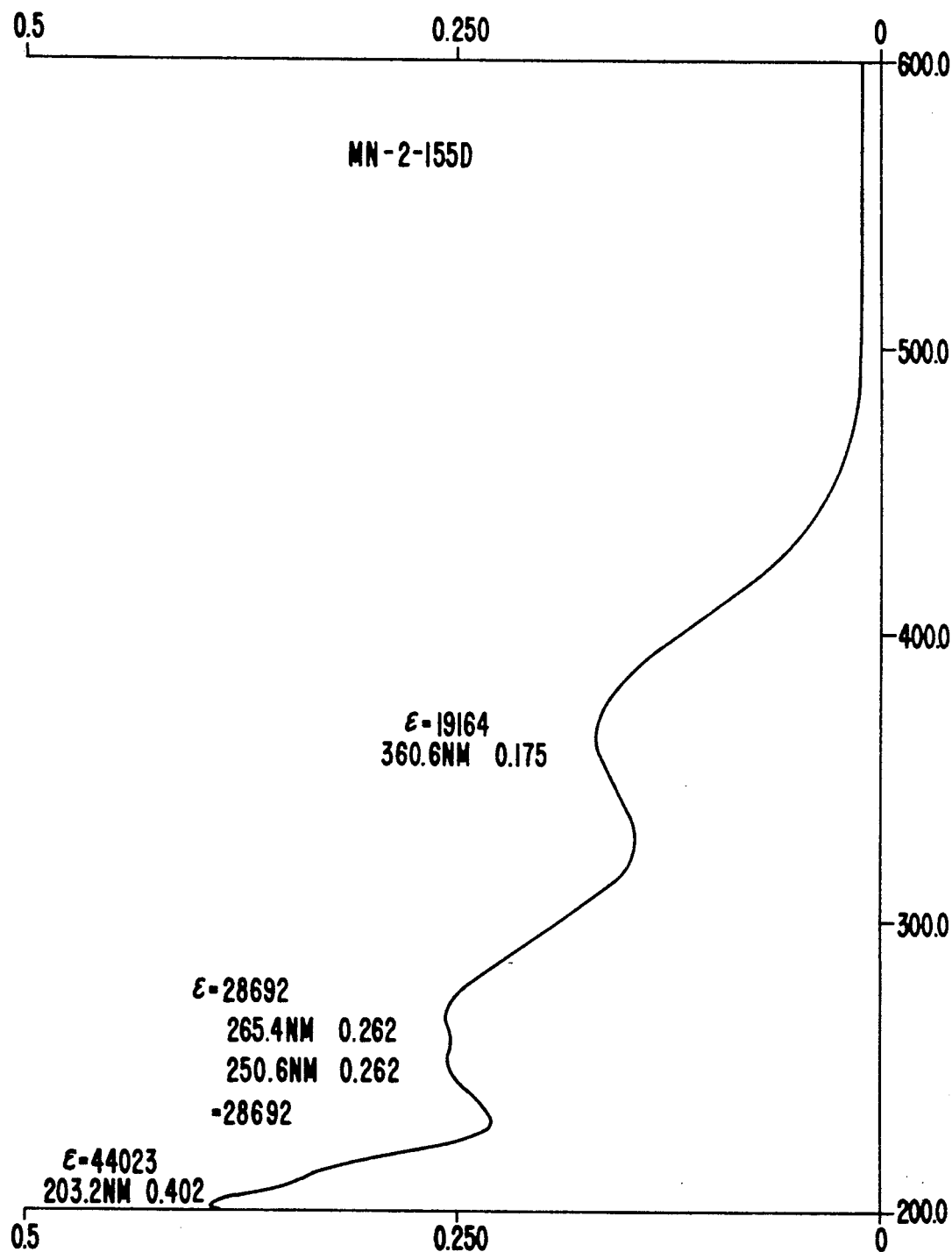
Figure 13:
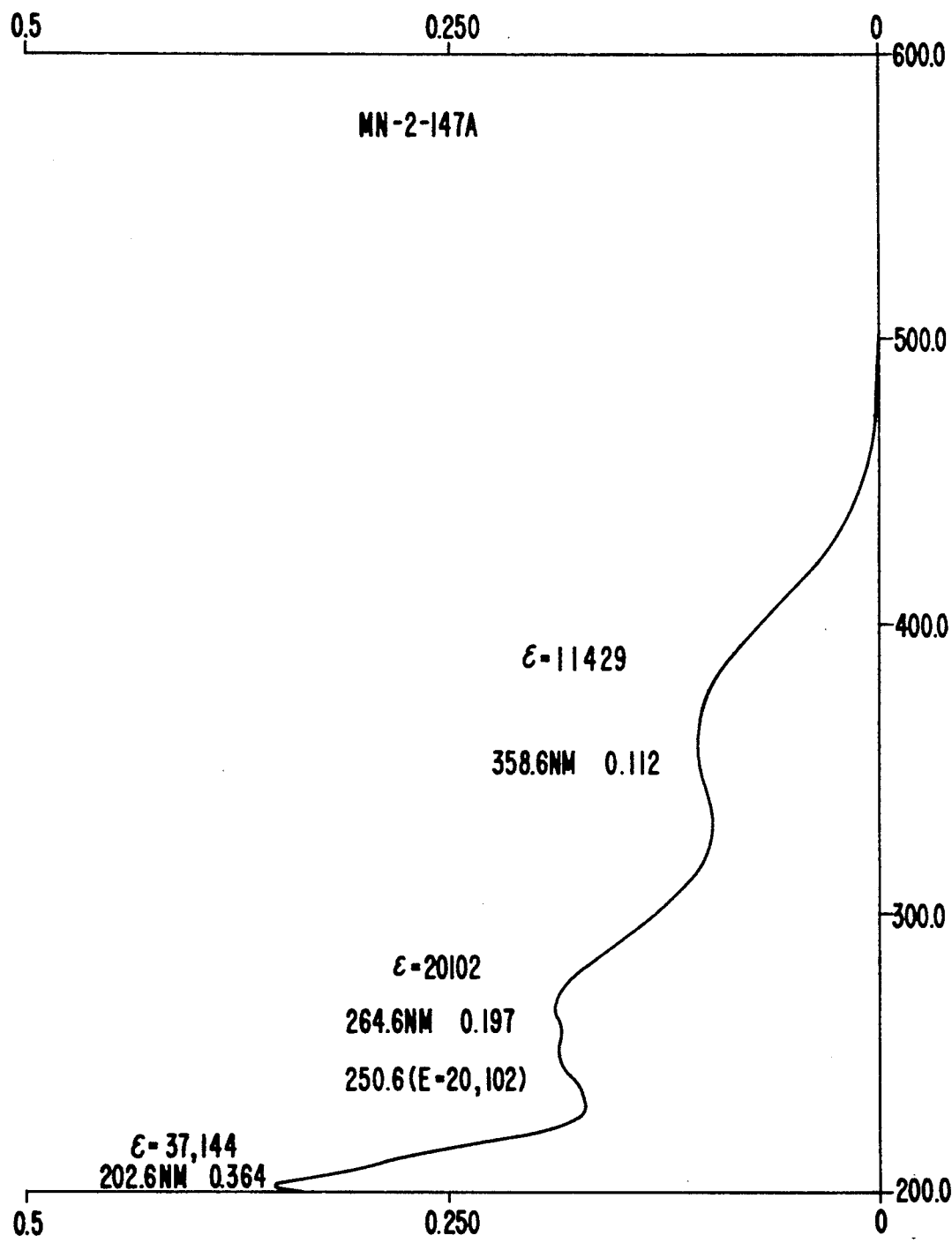
Figure 14:
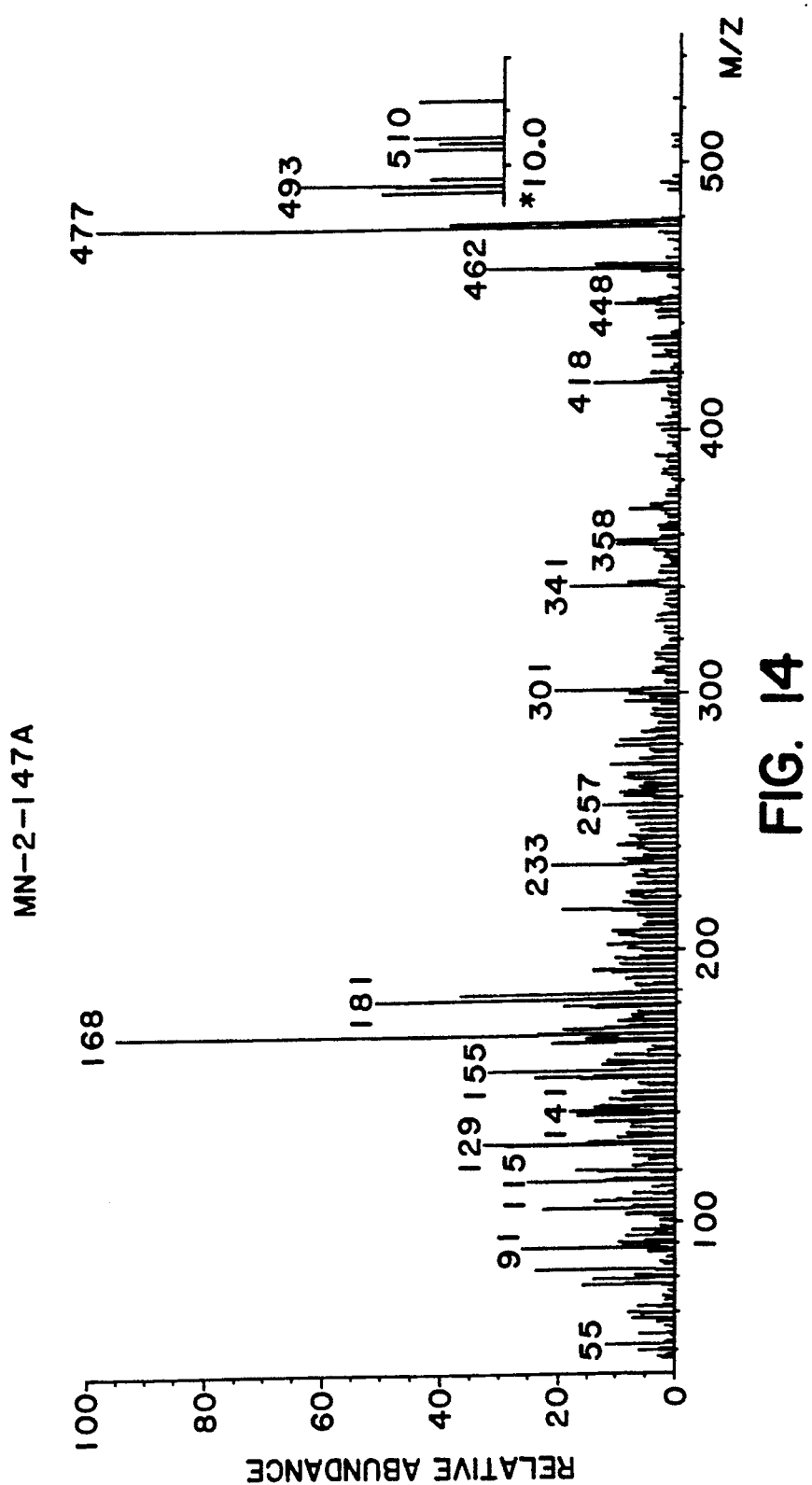
FIGS. 14 to 17 are the mass spectra for the nitrophenyl pyrones of Examples 1 to 4.
Figure 15:
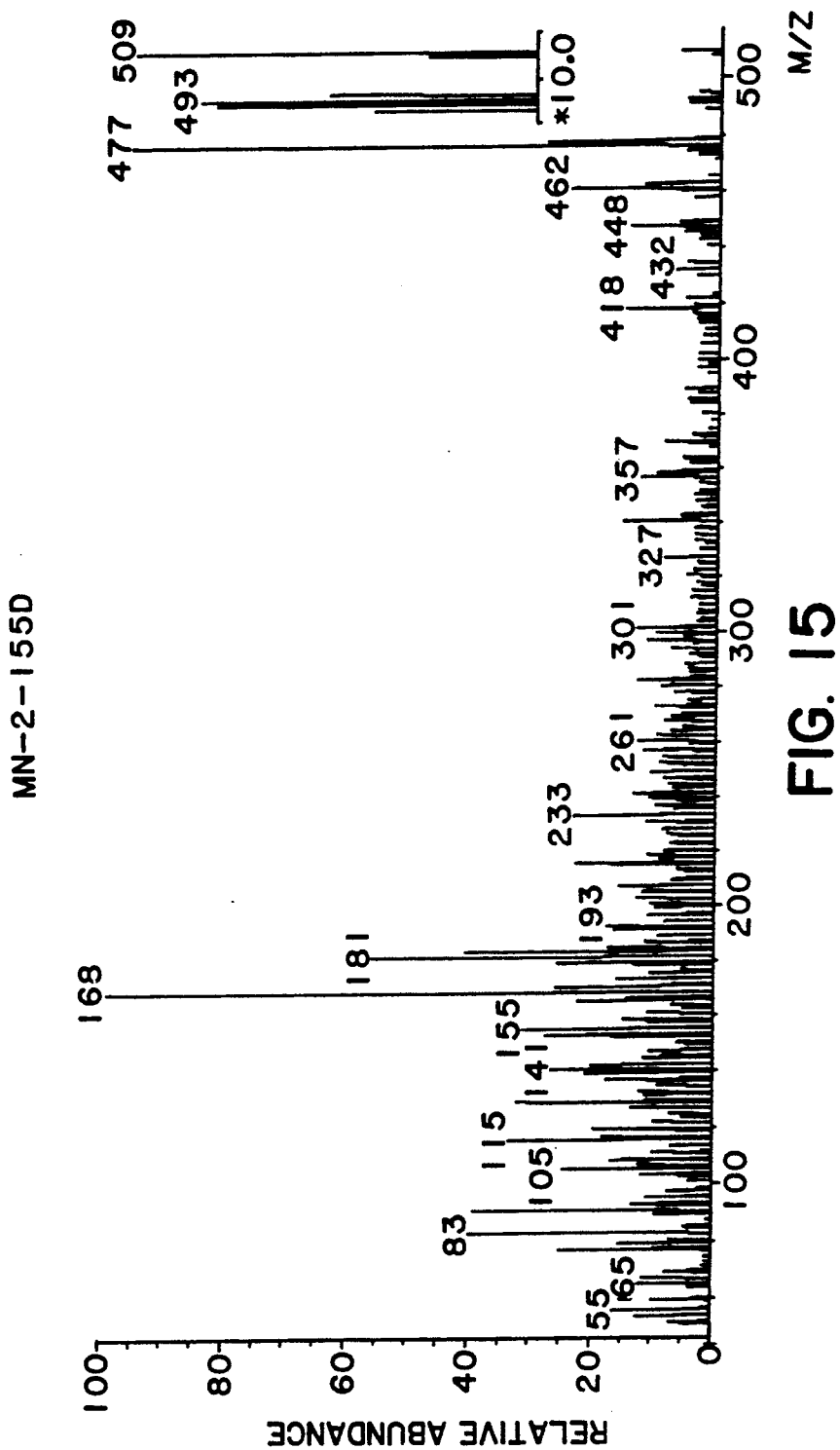
Figure 16:
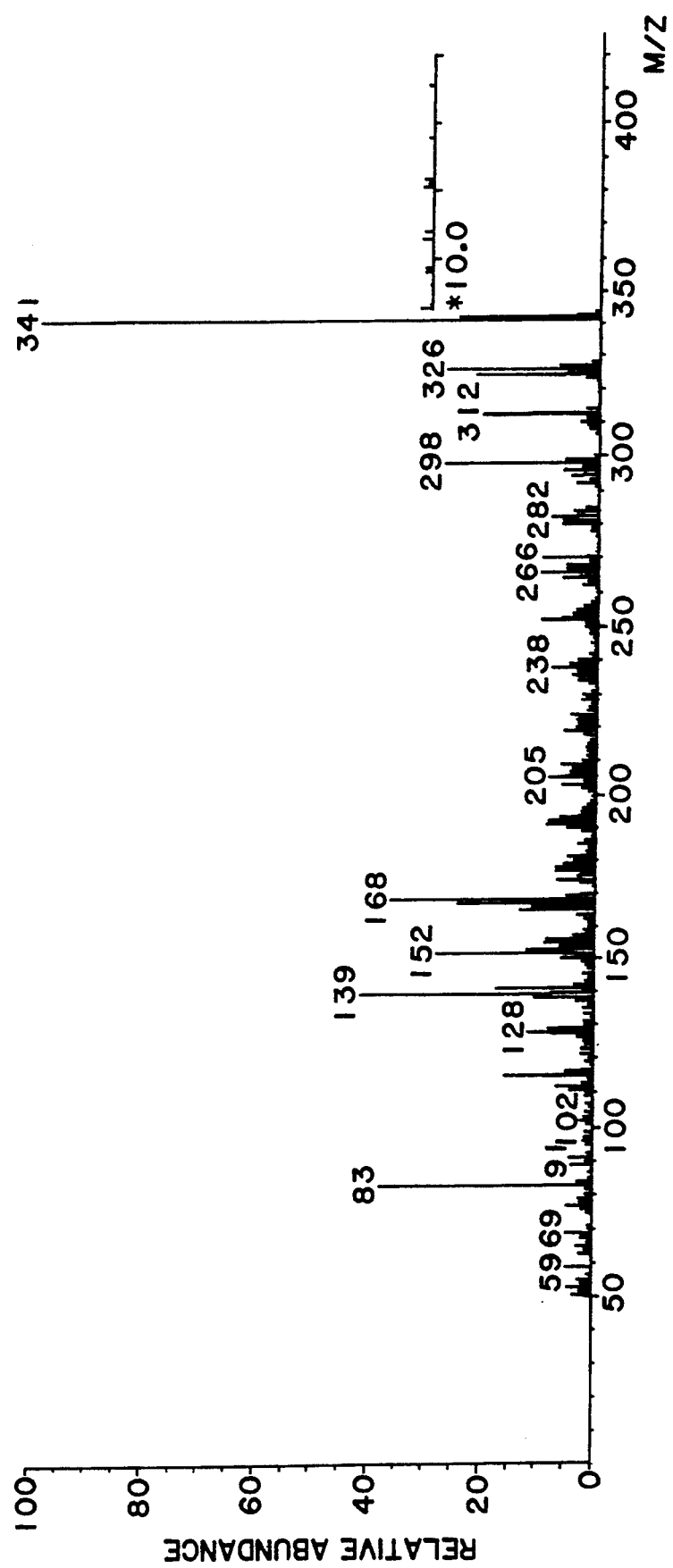
Figure 17:
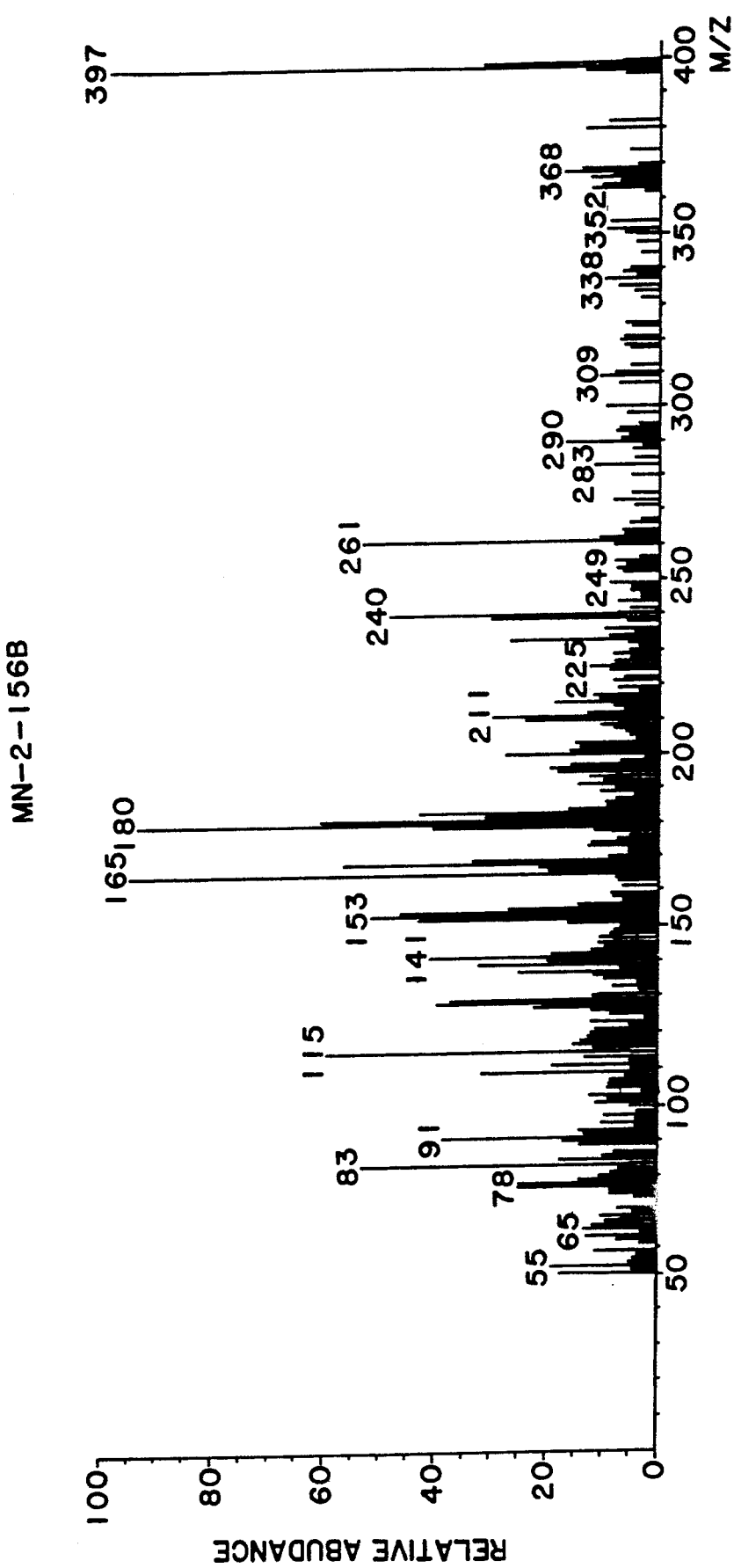

The present invention relates to a method for controlling an insect which comprises exposing the insect to an effective amount of a nitrophenyl $(CH=C)_x$R-pyrone, with CH$_3$ substituent, wherein x is an integer between 0 and 8 and R is selected from the group consisting of a direct bond, —CH=CH— and —CH= cyclic substituents containing 5 to 6 carbon atoms.

In particular the present invention relates to a method for controlling an insect which comprises exposing the insect to an effective amount of a compound selected from the group consisting of spectinabilins, aureothin, luteoreticulin, griseulin and isomers thereof produced by a Streptomyces sp..

Further, the present invention relates to the a composition for controlling insects which comprises:

(a)

a nitrophenyl $(CH=C)_xR_1$— with CH$_3$ substituent nitrophenyl pyrone wherein x is an integer between 0 and 8 and wherein R is selected from the group consisting of a direct bond, —CH=CH— and —CH= cyclic substituents containing 5 to 6 carbon atoms; and (b) an agricultural carrier other than water alone, wherein the nitrophenyl pyrone is present in an amount between about 0.001 and 100 ppm in the carrier sufficient to control the insect.

In particular the present invention relates to a composition for controlling insects which comprises:

(a) a compound selected from the group consisting of spectinabilins, aureothin, luteoreticulin and griseulin and isomers thereof; and (b) an agricultural carrier other than water alone, wherein the aureothin is present in an amount between about. 0.001 and 100 ppm in the carrier sufficient to control the insect.

Finally the present invention relates to a novel compound of the formula

[chemical structure: O$_2$N-phenyl-CH$_2$-C(CH$_3$)=CH-CH=CH-pyrone ring with CH$_3$, OCH$_3$, CH$_3$ substituents]

The nitrophenyl pyrones of the present invention are particularly effective against nematodes and mosquito larvae which are traditionally very difficult to kill. They can also be useful against other insects. The nitrophenyl pyrones of the present invention are particularly used in amounts between about 0.001 and 100 ppm which are insecticidally effective.

The nitrophenyl pyrone can be applied to the plant material, e.g. either to the seed or a propagule. Preferably the nitrophenyl pyrone is coated on the seed using an adhesive such as methyl cellulose, which is compatible with plant growth. The nitrophenyl pyrone can also be impregnated into the seed.

The nitrophenyl pyrone can be applied in a liquid agricultural carrier with a dispersant which maintains the nitrophenyl pyrone in solution in an amount between about 0.001 and 100 micrograms per ml to deliver about 0.001 and 100 ppm to the insect. Preferred dispersants are lower alkanols, particularly methanol, with various surfactants including anionic and cationic surfactants. Other organic solvents can be used to form emulsions of the nitrophenyl pyrone in water. The nitrophenyl pyrones can be provided in a solid mixture including the dispersant and the nitrophenyl pyrone. The composition can be formulated in solid carriers which aid in dispersing the nitrophenyl pyrone in the soil or planting material. The nitrophenyl pyrone is present in an amount in the solid carrier which provides between about 1 and 100 micrograms by weight of the solid carrier.

The nitrophenyl pyrones can be formulated as wettable powders, flow concentrates, emulsifiable concentrates, granular formulations and the like.

Wettable powders can be prepared by grinding together about 20% to 45% by weight of a finely divided carrier such as kaolin, bentonite, diatomaceous earth, attapulgite, or the like, 45% to 80% by weight of the nitrophenyl pyrone, 2% to 5% by weight of a dispersing agent such as sodium lignosulfonate, and 2% to 5% by weight of a nonionic surfactant, such as octylphenoxy polyethoxy ethanol, nonylphenoxy polyethoxy ethanol or the like.

A typical flowable liquid can be prepared by admixing about .40% by weight of the nitrophenyl pyrone with about 2% by weight of a gelling agent such as bentonite, 3% by weight of a dispersing agent such as sodium lignosulfonate, 1% by weight of polyethylene glycol and 54% by weight of water.

A typical emulsifiable concentrate can be prepared by dissolving about 5% to 25% by weight of the active ingredient in about 65% to 90% by weight of N-methylpyrrolidone, isophorone, butyl cellosolve, methylacetate or the like and dispersing therein about 5% to 10% by weight of a nonionic surfactant such as an alkylphenoxy polyethoxy alcohol. This concentrate is dispersed in water for application as a liquid spray.

When the nitrophenyl pyrones are used for soil treatment, the compounds may be prepared and applied as granular products. Preparation of the granular product can be achieved by dissolving the nitrophenyl pyrone in a solvent such as methylene chloride, N-methylpyrrolidone or the like and spraying the thus prepared solution on a granular carrier such as corncob grits, sand, attapulgite, kaolin or the like.

The granular product thus prepared generally comprises about 3% to 20% by weight of nitrophenyl pyrone and about 97% to 80% by weight of the granular carrier. The nitrophenyl pyrones can also be mixed with herbicide or other pesticides which are applied to the plants or applied before or after the application of the herbicide or pesticide.

The Streptomyces strains used in the present invention are available from the American Type Culture Collection. They have been deposited by third parties and are available upon request. Numerous such strains are available from the ATCC and can be tested for the production of the nitrophenyl pyrones which are a distinct class of compounds. *Streptomyces griseus* var autotrophicus has been deposited as ATCC 53668 and produces compounds MN-2-147A and griseulin, a novel nitrophenyl pyrone, and aureothin, described hereinafter (Table 1). The strain produces faeriefungin as described in U.S. application Ser. No. 07/177,311. *Isolation and Growth.* ATCC 53668 was isolated from a soil sample collected from the center of a fairy ring. The soil was suspended in sterile physiological saline and serial dilutions were plated on various isolation media. The colony of this strain was picked up from a Czapeck agar plate (sucrose 20.0 g, NaNO$_3$ 3.0 g, K$_2$HPO$_4$ 1.0 g, MgSO$_4$.7H$_2$O0.5 g, KCl 0.5 g, FeSO$_4$.7H$_2$O 0.01 g, bacto agar 15.0 g, distilled water liter). The microorganism grows well at room temperature (25° C.) on most of the laboratory media. On YMG agar (yeast extract, malt extract, glucose, agar; 4:10:4:18 grams per liter in distilled water), it produced slightly wrinkled colonies that were yellowish orange with abundant aerial hyphae at the periphery. The growth was powdery on N.Z. Amine-A (NZ amine-A 3 g in liter distilled water) agar and leathery on nutrient agar (Difco, Detroit, Mich.). Older colonies developed cracks typical of *Nocardia autotrophica*. During the microscopic examination, the aerial as well as substrate hyphae appeared straight with branchings at right angles. Spirals, sporangia, spore chain or endospores were not seen. The microorganism decomposed adenine, tyrosine, hypoxanthine, xanthine, and casein. It produces acid with adonitol, cellobiose, glucose, galactose, inositol, lactose, maltose, mannitol, melibiose, a-methyl-D-glucoside, raffinose, trehalose, and xylose. Acid production was not observed with arabinose, erythritol, melezitose, rhamnose, and sorbitol.

Although the colonial morphology of ATCC 53668 was similar to that of *N. autotrophica*, its physiological characteristics were closer to those of *Streptomyces griseus*. Consideration of these two major traits warranted recognition of this strain as a new variety of *S. griseus*. The nomenclature, *S. griseus* var. autotrophicus var. nov. was adopted.

SPECIFIC DESCRIPTION

The following Examples 1 to 6 show the preparation, identification and testing of the nitrophenyl pyrone compounds used in the method of the present invention. The method used herein is by means of fermentation using various species of Streptomyces.

EXAMPLE 1

MN-2-147A, . MN-2-156A and MN-2-156B nematocidal/mosquitocidal compounds were isolated and purified from the fermentation broth of *S. griseus* var. autotrophicus ATCC 53668 as shown in FIG. 1. Modifications in the fermentation medium and conditions for *S. griseus*, a previously reported isolate which produces faeriefungin antibiotic in Ser. No. 177,311, resulted in the production of MN-2-147A. Less molasses was used in the regular A-9 medium to obtain the modified A-9 medium (A-9 regular, Peptone 5g, glucose 10g, molasses 20g/L; modified A-9, peptone 5g, glucose 10 g and molasses 10-15 g/L). Fermentation was carried out in a modified Bellco 15 L glass fermentor (two side baffles opposite to each other on the side of the fermentation flask). The fermentation conditions were: 7 days, 26° C., air flow 40 psi, stirrer speed 800–900 rpm, 1 ml silicone oil anti-foam added twice at 24 hour and 12 hour intervals. The processing of MN-2-147A was as shown in FIG. 1.

MN-2-147A was isolated as an orange-yellow solid, recrystallized from MeOH, gave melting point at 74°–75° C. (reported closely related spectinabilin has a melting point 91°–92° C.); UV maxima at 365 (7528), 267 (9788), 251 (9747), 212 (12692) and 202 (16943) nm in EtOH. The reported UV maxima for spectinabilin 367 (15,500), 268 (18200), 252 (17600), 218 (19100) nm in EtOH. The extinction values for MN-2-147A were about half the extinction values for spectinabilin. $^1$H and $^{13}$C-NMR spectra indicated MN-2-147A and MN-2-155D, isolated from Streptomyces spectinabilis, are optical isomers. The compound MN-2-147A was identified to have the structure as follows:

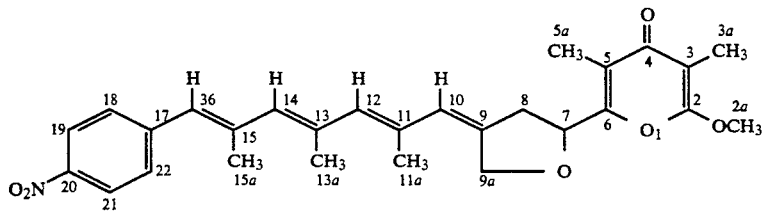

EXAMPLES 2 TO 4

In a like manner nitrophenyl pyrones MN-2-155D, MN-2-156A and MN-2-156B were isolated from strains of Streptomyces obtained from the American Type Culture Collection (ATCC) as follows:
Streptoverticillium mobaraense ATCC 25365
Streptomyces spectinabilis ATCC 27465
and the nitrophenyl pyrones isolated using the method set forth in FIG. 1 and in Example 1. The compounds isolated were as shown in Table 1.

TABLE 1

List of Streptomyces strains and metabolites, the nitrophenyl pyrones and nematocidal and mosquitocidal activities when fermented in A-9 medium.

|  | 147A | 155D | 156A | 156B |
|---|---|---|---|---|
| Streptomyces griseus var autotrophicus ATCC 53668 | * | — | * | * |
| Streptomyces luteoreticuli, ATCC 25365 (Streptoverticillium mobaraense) | — | — | * | * |
| Streptomyces spectinabilis, ATCC 27465 | — | * | — | — |
| Streptomyces nigellus subsp. africanus, ATCC 31496 | — | — | — | — |
| Streptomyces nigellus, ATCC 27450 | — | — | — | — |

Table 2 shows the nematocidal activity of the crude extracts obtained by the method of FIG. 1.

TABLE 2

| Nematocidal activity of crude extracts (3h) Concentration in μg/ml | | | | | |
|---|---|---|---|---|---|
|  | 1 | 4 | 40 | 80 | 160 |
| 27465A | — | — | * | ** | all dead |
| 27465B | — | — | — | — | — |
| MN-2-147A | all dead | all dead | all dead | all dead | all dead |
| 25365 | — | — | all dead | all dead | all dead |
| Control | — | — | — | — | — |

— no activity
* 30% dead
** 60% dead

EXAMPLE 4

Based upon the results of the tests shown in Table 2, the compounds 155D, 156A and 156B were identified based upon $^1$H-NMR, $^{13}$C-NMR, melting point, ultraviolet spectra and mass spectra. The data for the identification of Compound MN-2-147A is also set forth. The results are shown in Tables 3 to 5 and in FIG. 2 to 7.

TABLE 3

$^1$H-NMR Chemical Shift Values and Their Assignments

| MN-2-155D | MN-2-147A | Multiplicity | Assignment |
|---|---|---|---|
| 8.16 | 8.14 | d, J=9Hz | 19, 21 |
| 7.43 | 7.38 | d, J=9Hz | 18, 22 |
| 6.45 | 6.41 | s | 16 |
| 6.07 | 6.03 | s | 10 |
| 5.95 | 5.91 | s | 14 |
| 5.83 | 5.78 | s | 12 |
| 5.11 | 5.07 | t, J=6.6Hz | 7 |
| 4.76 | 4.66 | qb, J=13Hz | 9a |
| 3.93 | 3.87 | s | 2a |
| 2.97 | 2.85 | dq, J=6.4, 15.7Hz | 8 |
| 2.08 | 2.04 | s | 15a |
| 2.03 | 1.98 | s | 13a |
| 2.02 | 1.94 | s | 5a |
| 1.99 | 1.92 | s | 11a |
| 1.84 | 1.76 | s | 3a |

| MN-2-156A | | | MN-2-156B | | |
|---|---|---|---|---|---|
| ppm | multiplicity | assignment | ppm | multiplicity | assignment |
| 8.19 | d, J=9Hz | H-13, H-15 | 8.15 | d, J=9, dHz | H-15, H-17 |
| 7.45 | d, J=9Hz | H-12, H-16 | 7.36 | d, J=9Hz | H-14, H-18 |
| 7.1 | s | H-10 | 6.33 | s | H-12 |
| 6.57 | s | H-7 | 6.17 | s | H-10 |
| 6.25 | s | H-8 | 5.11 | t, J=6.2Hz | 7 |
| 3.93 | s | 4a | 4.76 | q, b, J=13Hz | 9a |
| 2.14 | s | 9a | 3.91 | s | 2a |
| 2.11 | s | 5a | 2.97 | dq, J=6.4, 15.7Hz | 8 |
| 1.95 | s | 3a | 2.00 | s | 5a |
|  |  |  | 1.99 | s | 11a |
|  |  |  | 1.80 | s | 3a |

TABLE 4

$^{13}$C-NMR Chemical Shifts and Their Assignments

| Position | MN-2-155D | MN-2-147A |
|---|---|---|
| 4 | 181.26 | 180.47 |
| 2 | 162.73 | 162.00 |
| 6 | 155.68 | 155.03 |
| 20 | 146.52 | 145.70 |
| 17 | 145.32 | 144.61 |
| 15 | 140.02 | 139.33 |
| 9 | 138.40 | 137.64 |
| 13* | 136.25 | 135.54 |
| 12 | 135.94 | 135.19 |
| 14 | 135.03 | 134.28 |
| 11* | 134.57 | 133.83 |
| 18 | 130.16 | 129.41 |
| 22 | 130.12 | 129.40 |
| 16 | 128.79 | 128.01 |
| 10 | 127.42 | 126.72 |
| 19 | 124.19 | 123.39 |
| 21 | 124.10 | 123.36 |
| 5 | 120.61 | 119.78 |
| 3 | 100.57 | 99.74 |
| 7 | 77.24 | 73.11 |
| 9a | 73.84 | 69.98 |
| 2a | 55.90 | 55.16 |
| 8 | 38.88 | 38.11 |
| 13a | 20.27 | 19.48 |
| 15a | 20.13 | 19.34 |
| 11a | 18.51 | 17.72 |
| 5a | 10.08 | 9.31 |

TABLE 4-continued

13C-NMR Chemical Shifts and Their Assignments

| 3a | | 7.56 | | 6.80 |
|---|---|---|---|---|
| Position | MN-2-156A | | Position | MN-2-156B |
| 4 | 166.28 | | 4 | 181.20 |
| 2 | 165.35 | | 2 | 162.73 |
| 6 | 160.24 | | 6 | 155.33 |
| 14 | 146.88 | | 16 | 146.66 |
| 11 | 144.50 | | 13 | 144.91 |
| 9 | 139.08 | | 11 | 141.31 |
| 8 | 136.52 | | 10 | 141.30 |
| 7 | 131.36 | | 9 | 139.29 |
| 12 | 130.42 | | 14 | 130.25 |
| 16 | 130.40 | | 18 | 130.21 |
| 10 | 127.69 | | 12 | 128.97 |
| 13 | 124.25 | | 15 | 126.63 |
| 15 | 124.23 | | 17 | 124.17 |
| 5 | 103.67 | | 5 | 120.77 |
| 3 | 94.16 | | 3 | 100.56 |
| 4a | 56.86 | | 7 | 73.93 |
| 9a | 19.82 | | 9a | 70.75 |
| 5a | 14.96 | | 2a | 55.92 |
| 3a | 9.40 | | 8 | 38.87 |
| | | | 11a | 18.37 |
| | | | 5a | 10.08 |
| | | | 3a | 7.54 |

*Assignments can be interchanged.

TABLE 5

| | m.p. |
|---|---|
| MN/2/155D | 107–102° C. |
| MN/2/156A | 164–165° C. |
| MN/2/156B | 157–158° C. |
| MN/2/147A | 74–75° C. |

Based upon this data, the following structures were determined.

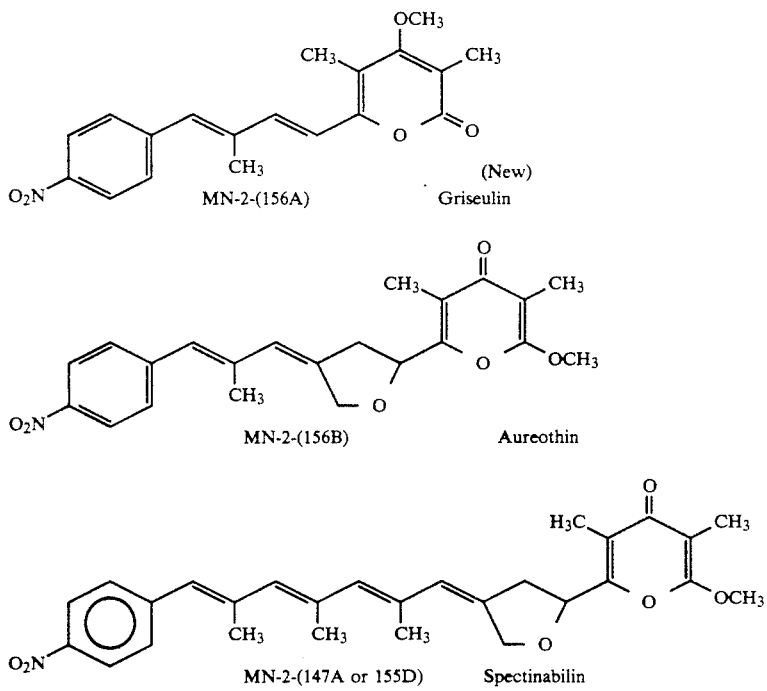

MN-2-(156A) (New)
Griseulin

MN-2-(156B)
Aureothin

MN-2-(147A or 155D)
Spectinabilin

Compound MN-2-156A is a new compound which has not been described in the literature. It does not contain the furanyl group which is present in aureothin and spectinabilin. It is noted that the new spectinabilin (147A) has a much different melting point than the reported spectinabilin (155D). It was concluded that compound 147A was an optical isomer of spectinabilin.

EXAMPLE 5

The nematocidal activity of the purified compounds of Examples 1 to 4 was determined. The results are shown in Table 6.

TABLE 6

| Nematocidal activity of the *Streptomyces* metabolites | | | | |
|---|---|---|---|---|
| Concentration in ppm | 147A | 155D | 156A | 156B |
| 10 | D | D | D | D |
| 1 | D | D | 90% D | D |
| 0.1 | 90% D | slow | 90% D | 90% D |
| 0.01 | Ok | Ok | adults D young Ok | Ok |
| CTL | Ok | Ok | Ok | Ok |

D = 100% kill. Ok = no effct. CTL = control.
At 24 hours (0.1 ppm.) all the test compounds gave 100% mortality. At 0.1 ppm some young nematodes were alive for 155D and 147A at 24H. The above experiment was conducted in triplicate. Nematodes used were: *C. elegans, P. redivirus,* and *H. glycines*.

EXAMPLE 6

The mosquitocidal activity of the compound of Examples 1 to 4 was determined. The results are shown in Table 7.

TABLE 7

| Mosquitocidal activity of *Streptomyces* metabolites. | | | | |
|---|---|---|---|---|
| Concentration in ppm | 147A | 155D | 156A | 156B |
| 62.5 | D | 60% D | D | D |
| 6.25 | D | 80% D | 60% D | D |
| CTL | O | O | O | O |

D = 100% killed. At 24 hours, 155D and 156A gave 100% kill. The mosquito larvae used were *Aedes egyptii*.

Table 6 shows that the compounds of Examples 1 to 4 are particularly effective on nematocides in the range between 0.01 and 10 ppm. Table 7 shows that the compounds of Examples 1 to 4 are particularly effective at dosages between abut 6 and 63 ppm. Effective dosages between about 0.001 and 100 ppm are preferred for the compounds of Examples 1 to 4. As can be seen, there are different activities for the compounds within this range.

It will be apparent from the differences in the claimed structures of the isolated nitrophenyl pyrones that there are a wide variety of such compounds that are effective as insecticidal compounds. Numerous compounds will occur to those skilled in the art which can be derived synthetically rather than by the use of microorganisms.

It is intended that the foregoing description be only illustrative of the present invention and that the present invention be limited only by the hereinafter appended claims.

I claim:

1. A method for killing an insect which comprises exposing the insect to an effective amount of

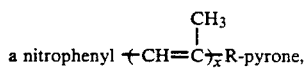
a nitrophenyl $(CH=C)_{\overline{x}} R$-pyrone, wherein x is an integer between 0 and 8 and R is selected from the group consisting of a direct bond, —CH=CH— and —CH= furanyl.

2. The method of claim 1 wherein the pyrone is

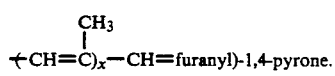
nitrophenyl$(CH=C)_x$—CH=furanyl-dimethyl-methoxy pyrone.

3. The method of claim 1 wherein the pyrone is a 2-methoxy-3,5-dimethyl-6-(p-nitrophenyl

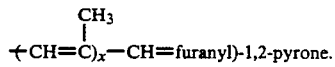
$(CH=C)_x$—CH=furanyl)-1,4-pyrone.

4. The method of claim 1 wherein the pyrone is a 4-methoxy-3,5-dimethyl-6-(p-nitrophenyl)-

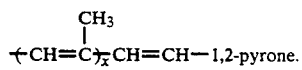
$(CH=C)_x$—CH=furanyl)-1,2-pyrone.

5. The method of claim 1 wherein the pyrone is methoxy-3,5-dimethyl-6-(p-nitrophenyl)-

$(CH=C)_{\overline{x}}CH=CH$—1,2-pyrone.

6. The method of claim 1 wherein the nitrophenyl pyrone is selected from the group consisting of

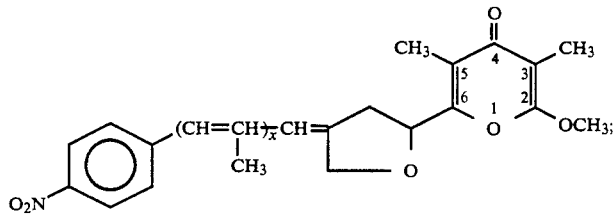

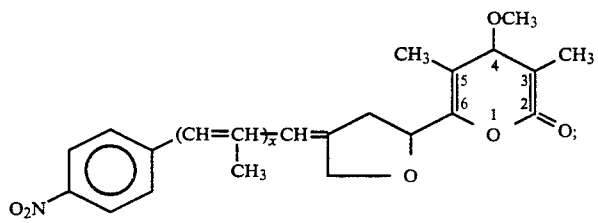

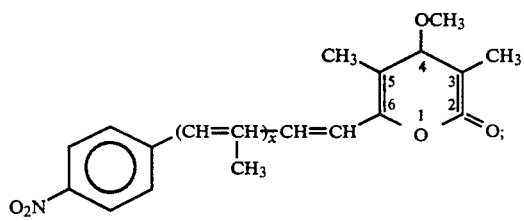

and

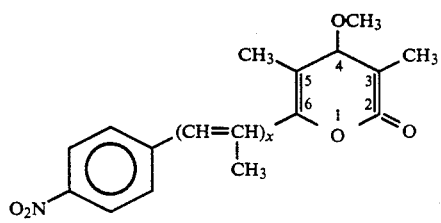

7. The method of claim 1 wherein the insect is exposed to an amount between about 0.001 and 100 ppm by weight of the compound.

8. A method for killing an insect which comprises exposing the insect to an effective amount of a compound selected from the group consisting of spectinabilin, aureothin, luteoreticulin, griseulin and isomers thereof to kill the insect.

9. The method of claim 8 wherein the compound is spectinabilin.

10. The method of claim 8 wherein the insect is in a soil.

11. The method of claim 8 wherein the insect is mosquito larvae.

12. The method of claim 11 wherein the mosquito larvae is *Aedes egyptii*.

13. The method of claim 12 wherein the larvae are dispersed in a pool of water to which the compound is applied.

14. The method of claim 8 wherein the insect is exposed to an amount between about 0.001 and 100 ppm by weight of the compound.

* * * * *

UNITED STATES PATENT AND TRADEMARK OFFICE
CERTIFICATE OF CORRECTION

PATENT NO. : 5,236,949

DATED : August 17, 1993

INVENTOR(S) : Muraleedharan G. Nair

It is certified that error appears in the above-indentified patent and that said Letters Patent is hereby corrected as shown below:

Column 1, line 26, "Kovama" should be --Koyama--.

Column 4, line 10, after "water" and before "liter", --1-- should be inserted.

Column 4, line 17, after "in" and before "liter", --1-- should be inserted.

Column 9 (Claim 1) line 27, after "furanyl", --to kill the insect-- should be inserted.

Column 10 (Claim 5) line 23, "methoxy-3-" should be -- 4-methoxy-3- --.

Column 10 (Claim 6), in the last three structures, the bonds in the last ring should be as follows:

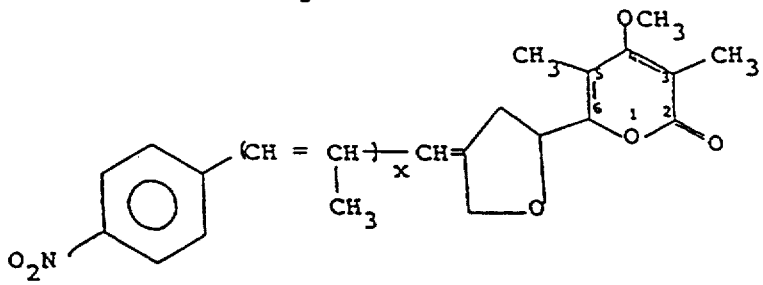

UNITED STATES PATENT AND TRADEMARK OFFICE
CERTIFICATE OF CORRECTION

PATENT NO. : 5,236,949

DATED : August 17, 1993

INVENTOR(S) : Muraleedharan G. Nair

It is certified that error appears in the above-indentified patent and that said Letters Patent is hereby corrected as shown below:

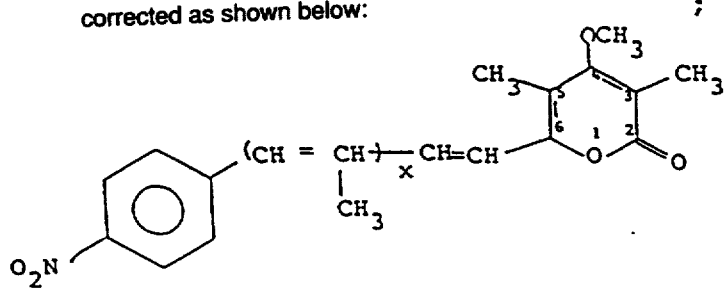 ;

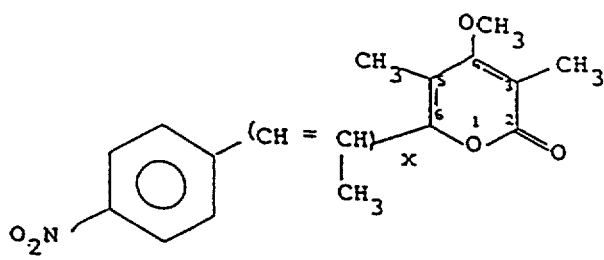 ; and

Signed and Sealed this

Twenty-fifth Day of October, 1994

Attest:

BRUCE LEHMAN

Attesting Officer  Commissioner of Patents and Trademarks